United States Patent [19]

Collins

[11] Patent Number: 4,803,989
[45] Date of Patent: Feb. 14, 1989

[54] FULL WIDTH METATARSAL PAD

[76] Inventor: Jack N. Collins, 2875 Joyce St., Fayetteville, Ark. 72703

[21] Appl. No.: 152,994

[22] Filed: Feb. 8, 1988

[51] Int. Cl.$^4$ ............................. A61F 5/14; A43B 7/14
[52] U.S. Cl. ...................................... 128/586; 128/595
[58] Field of Search ............... 128/595, 586, 623, 621, 128/615

[56] References Cited

U.S. PATENT DOCUMENTS

| | | | |
|---|---|---|---|
| 1,814,514 | 7/1931 | Karlson | 128/623 |
| 1,841,942 | 1/1932 | Fenton | 128/586 |
| 1,850,977 | 3/1932 | Masebeck | 128/586 |
| 1,890,910 | 12/1932 | Marshall | 128/595 |
| 2,089,384 | 8/1937 | Levitt | 128/586 |
| 2,486,653 | 11/1949 | Hukill | 128/615 |
| 2,613,456 | 10/1952 | Amico | 128/621 |
| 2,863,231 | 12/1958 | Jones | 128/586 |

FOREIGN PATENT DOCUMENTS

| | | | |
|---|---|---|---|
| 514063 | 12/1930 | Fed. Rep. of Germany | 128/595 |
| 2063926 | 7/1971 | Fed. Rep. of Germany | 128/586 |
| 360302 | 11/1931 | United Kingdom | 128/586 |

Primary Examiner—Edgar S. Burr
Assistant Examiner—Tonya Lamb
Attorney, Agent, or Firm—Robert R. Keegan

[57] ABSTRACT

Metatarsal pad structured with relation to the foot for which it is intended so that it bridges across the width of the five metatarsal bones; a configuration at the front is such that each metatarsal is supported just posteriorly of the head thereof and with a height to raise the heads of the metatarsals from weight bearing and transfer of the weight over a larger area. The front of the pad is characterized by a radius of curvature of about 3/16 of an inch in the vertical plane and the frontal outline in the horizontal plane is preferably convex in the central portion while being slightly concave on either side thereof; this conforms to the shape of volar surface of the metatarsal as it develops the head of each metatarsal. The alternate concave and convex frontal outlines follow a line just posterior to the head of the first metatarsal and progressing laterally just behind the head of each subsequent metatarsal. The pads are asymmetric and are provided for the left and the right foot. A minimum of about five sizes are provided for adult foot sizes. The pads may be formed of room temperature curing urethane elastomer or injection molded latex or other suitable material, preferably with flexibility, resilience and relatively low compressibility. It is contemplated that the pads will be fitted by properly trained persons for maximum benefit in reducing trauma to the heads of the metatarsal that cause callosities and other problems.

20 Claims, 2 Drawing Sheets

FULL WIDTH METATARSAL PAD

The present invention relates to metatarsal pads for reducing trauma to the heads of the metatarsal, and more particularly to such pads as provided by the present invention which bridge across all five metatarsal bones supporting them posteriorly to the heads of the metatarsals to reduce bearing weight on the heads themselves. Preferably the pad of the present invention has its greatest height near the front edge, which viewed from above has a curvature convex in the center and outwardly partially concave to closely match the arch defined by the five metatarsal heads where they merge into the shanks of the metatarsal bones; thereby supporting each metatarsal just posteriorly of the head of the metatarsal. This configuration of the pad results in transferring the weight from the heads of the metatarsals over a larger area and more effectively reduces the trauma to the heads of the metatarsals which is known to cause callosities and other problems.

Since the human foot is asymmetric it follows that pads according to the invention are provided in left foot and right foot versions, and preferably in at least five sizes for adult feet and additional smaller sizes as may be required for children. Pads according to the invention not only provide relief of problems of the plantar surface of the metatarsal heads, but aid in preserving the normal metatarsal arch. The material of which they are formed is substantially incompressible at the pressures to which subjected, but is preferably resilient and flexible; room temperature curing urethane elastomer, or injected molded latex or balata are suitable materials, as are many other plastics.

Pads are preferably formed by molding in precisely dimensioned molds, and with suitable materials they will be quite durable and serviceable for a year or more in everyday use. Since the design of pads according to the invention is carefully devised to fit the bone structure of a user, their function is greatly enhanced when they are selected as to size and permanently placed in position in the shoe by a person properly trained or instructed in placement and use of the pads.

Pads for support of the foot have been proposed in many different variations, including pads which function in whole or in part to support the metatarsals of the foot. For the most part such foot pads did not contemplate supporting all five of the metatarsals and did not have the full width characteristic of the pads of the present invention.

In some cases it has been proposed to provide a pad which supports all five metatarsal bones to prevent them from falling as seen in U.S. Pat. No. 2,475,417 to John Wysowski, granted July 5, 1949, class 128-80. The Wysowski patent does not, however, provide a structure which carries out the stated objective efficaciously. The Wysowski pad is constructed of sponge rubber (column 1, line 39) and the upper surface of the pad merges with the base surface in a feather edge which extends entirely around the marginal edges of the pad (column 1, lines 41-44). The front edge of the pad is nearly straight for the most part, and convexly curved at the inner and outer portions. While it is stated that the pad is curved to conform to the curvature of the metatarsal bones of the several toes, the nature of curvature is inappropriate to give support just posteriorly of the heads of the metatarsal as accomplished by the present invention. In general, the specific structure shown in the drawings and described with reference to the drawings is not consistent with the object of providing a pad extending substantially entirely across the bottom of the foot.

Other prior patents make reference to supporting the metatarsals, but they will be found to lack full width support, or fail to provide support just posteriorly of each of the metatarsal heads with a height to raise the heads from weight bearing in the manner provided by the present invention. Representative of such metatarsal pads are found in U.S. Pat. No. 4,442,612 to Hauser, granted Apr. 17, 1984, class 36/43; U.S. Pat. No. 4,232,457 to Mosher, issued Nov. 11, 1980, class 36/44; U.S. Pat. No. 3,470,880 to Pagliano, issued Oct. 7, 1969, class 128-619; and U.S. Pat. No. 3,265,071 to Kirchner et al., issued Aug. 9, 1966, class 128-586.

In addition to providing the features and advantages described above, it is an object of the present invention to provide a metatarsal pad for a human foot formed of relatively incompressible material, the front edge of which is characterized by a small radius of curvature to a maximum height dimension less than one inch behind the front edge whereby each metatarsal is supported just posteriorly of the head at a height so as to substantially relieve weight bearing stress under the heads of the metatarsals.

It is another object of the present invention to provide such a metatarsal pad wherein the front, or most distal, surface is curved in such a manner not only to fit the width of the five metatarsals, but to conform to the shape of the volar under-surface of the metatarsal as it develops the head of each metatarsal.

It is still another object of the present invention to provide such a metatarsal pad wherein the front edge of the pad proceeds laterally just posterior to the head of the first metatarsal and to each subsequent head as it progresses from the inside to the outside of the foot, the curvature thus defined being convex in the central portion and concave in at least one lateral portion of the front edge of the pad.

It is yet another object of the present invention to provide such a pad wherein the height of the pad near the inside and outside edges is at least one-third the maximum height of the pad near the center thereof.

Other objects and advantages of the invention will be apparent from consideration of the following description in conjunction with the appended drawings in which.

Figure 1:
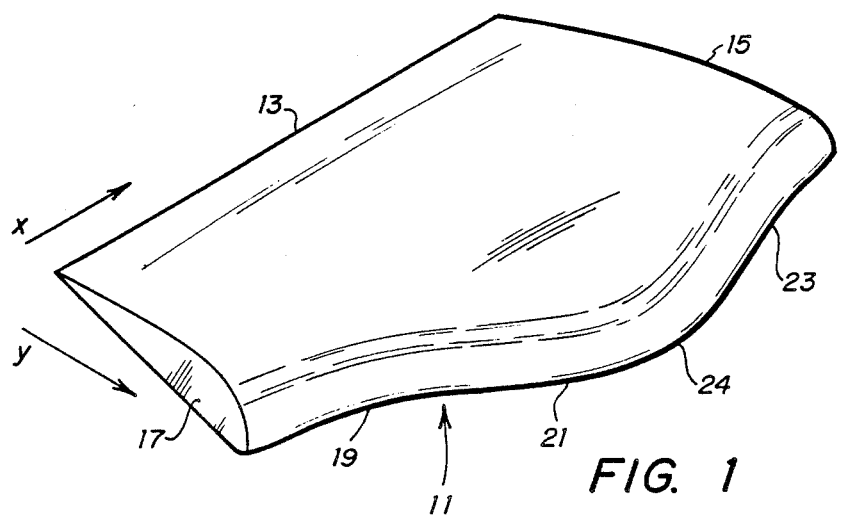
FIG. 1 is a view of computer generated contour lines of a pad according to the invention in isometric projection.
Figure 2:
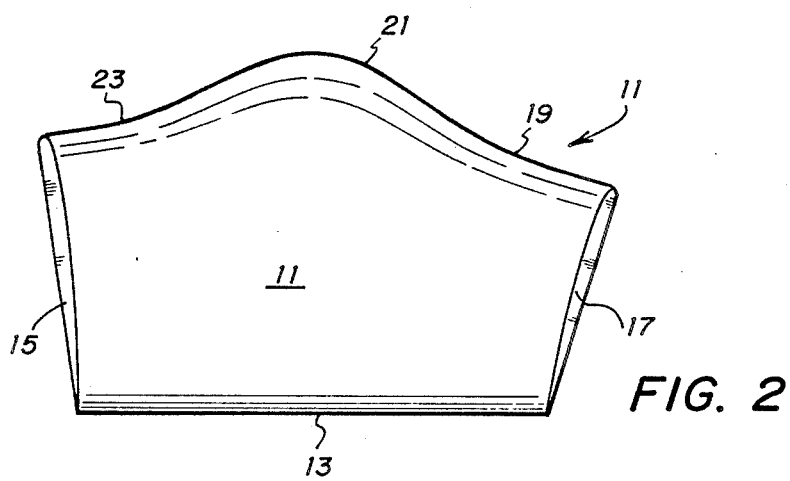
FIG. 2 is a top plan view thereof.

Referring now to the drawings, and particularly to FIGS. 1 through 4, a metatarsal pad 11 according to the invention is shown having a proper form to support the metatarsals of the right foot. A pad for the left foot would be the same except for a left-right reversal so that it would appear to be a mirror image of the illustration of FIG. 1.

The exact dimensions of the pad 11 are given in Table I which is included as an appendix hereto. As indicated by the arrows in FIG. 1 the y dimension is directed from the direction of heel-to-toe and the x dimension is directed from outside to inside; the z direction is vertical to complete the three mutually orthogonal axes. In Table I the points on the upper surface are designated by x, y, and z coordinates in that order. The bottom surface of the pad is essentially planar (z=0).

Since a close correspondence between the upper surface of the metatarsal pad and the metatarsals of the user's foot is very important, metatarsal pads of different sizes should be provided. Obviously the particular graduation of sizes is subject to variation, but it is convenient to correlate the metatarsal pad sizes with standard American shoe sizes. Furthermore, it has been found unnecessary to made gradations in pad size for each shoe size, and it is therefore preferred to let one pad size serve for two shoe sizes.

The preferred arrangement of pad sizing is to designate pad size No. 1 for shoe sizes 5–6, No. 2 for shoe sizes 7–8, No. 3 for shoe sizes 9–10, No. 4 for shoe sizes 11–12, and No. 5 for shoe sizes 13–14. Larger or smaller adult sizes may also be provided in a similar manner.

The pad of Table I with coordinates units in inches is a No. 3 pad for shoe sizes 9–10. The metatarsal pad is scaled up and down by allowing a difference in width of one-quarter inch per pad number (one-eighth inch per shoe size). For pad size Nos. 1–5 the lengths of the pad (y dimensions) are adjusted in proportion to change in the x dimension, but the heights in inches (z dimensions) are maintained as given in Table I. Such scaling will produce a correlation of pad width to adult shoe size of $W = 2\frac{1}{8} + S/8$ where W is width in inches and S is American shoe size.

Pads may also be provided for childrens' shoe sizes with the same quarter inch difference between pad numbers as to width, but a differential in height is also desirable for children's metatarsal pads, and it is preferred that there be a seven percent difference in height to correspond with each quarter inch difference in width.

Accommodations to the overall scheme may be made to allow for a user with left and right feet of substantially different length (different size pads may be employed for the left and right foot), and also it will be recognized that the width of the metatarsal pad is the most important dimension so that wide feet may require a larger size than a narrow or medium foot of the same length. Thus an E or wider foot may take a higher number pad while an A or narrower foot may take a lower number pad.

While the configuration of the pad illustrated in FIG. 1 is most precisely given in Table I, important features are shown in FIGS. 1-4 in more readily perceptible graphic form. Note, for example, that the rear edge 13 is preferably formed in a straight line and has been designated the y=0, z= line for Table I. Inside edge 15 and outside edge 17 are preferably straight, or slightly concave, and they diverge to conform generally to the shape of a shoe inner sole. In most cases the pad 11 when properly placed relative to the user's foot in the shoe will generally conform at edges 15 and 17 to the edges of the inside of the sole of the shoe. Such conformity is not essential, however, or edges 15 and 17 may be trimmed if desired.

The forward edge of the pad includes a concavely curved segment 19, a convex segment 21, and another slightly concave segment 23 in the preferred embodiment. Either concave segment 19 or concave segment 23 could, in some cases, be nearly straight and still achieve many of the advantages of the invention. The maximum length (y) dimension occurs at 24 near the mid-point of the x dimension, but slightly displaced toward the inside of the foot and the first metatarsal.

Figure 3:
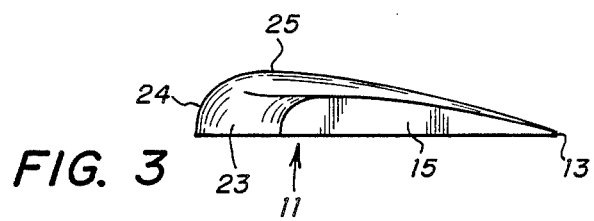
FIG. 3 is a left side elevational view thereof.

As been seen in FIG. 3 the front edge of the pad 11 rises almost vertically and curves with a relatively small radius of curvature (generally between 0.1 and 0.3 inches) to a maximum height at 25, much nearer the front edge 19, 21, and 23 of the pad 11 than the rear edge 13. Viewed as in FIG. 3 (or FIG. 6) the body has an airfoil-like shape.

Figure 4:
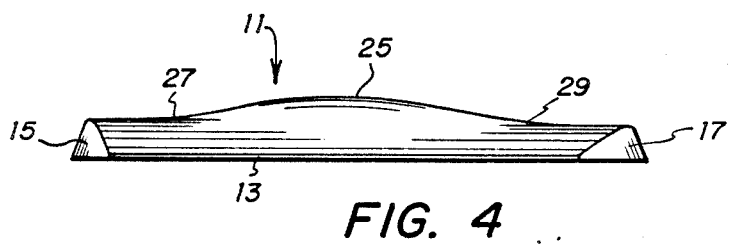
FIG. 4 is a rear elevational view thereof.

Viewing the pad from the rear in FIG. 4 it will be observed that the central curvature of the pad at 25 is convex, but there are very slightly concave portions at 27 and 29; the edge 15 and the edge 17 slope upward sharply at a slope of approximately 3-to-1. Thus the concave segments 27 and 29 have a height (z dimension) which is substantially more than half of the maximum height at 25.

It will be noted that from about the mid-point heel-to-toe of the pad 11 backwardly to the rearward edge 13 the pad has a gentle slope which essentially serves to cause the upper pad surface to flow smoothly into and join the insole of the user's shoe. Consequently the slope from the point of maximum height 25 to the rearward edge 13 could be more or less gradual with a corresponding change in the heel-to-toe dimension of the pad without materially affecting the operation of the pad. It is preferred, however, that the slope from the rear edge forward be gentle compared with the forward edge of the pad, and preferably this slope should be on the order of 0.25 or less.

Figure 5:
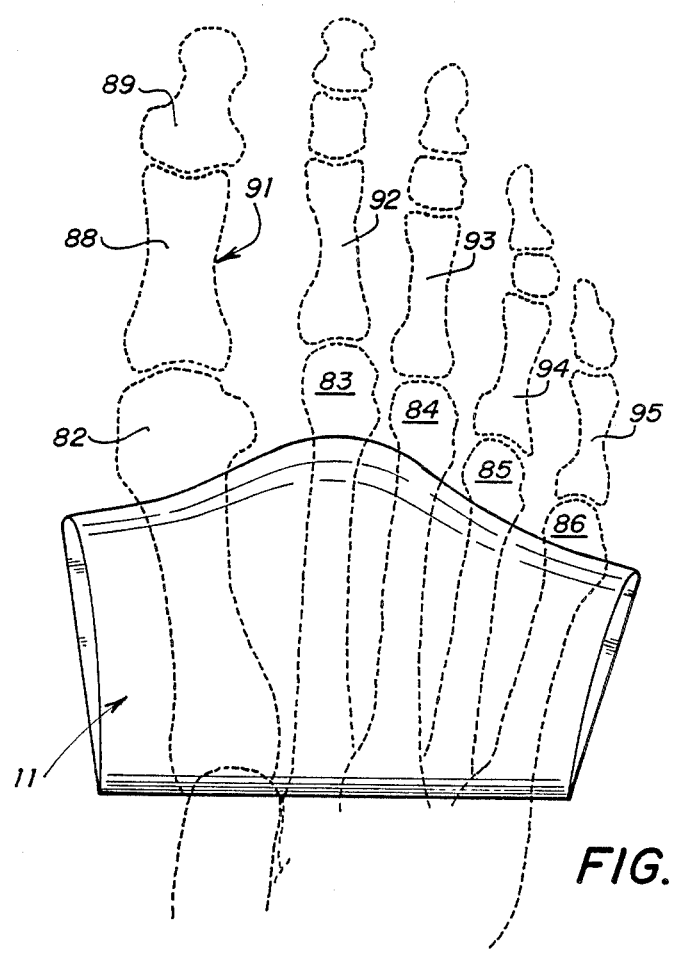
FIG. 5 is a top plan view showing the relation of a pad according to the invention to the bones of a human foot (shown in phantom lines) which it is selected to accommodate.
Figure 6:
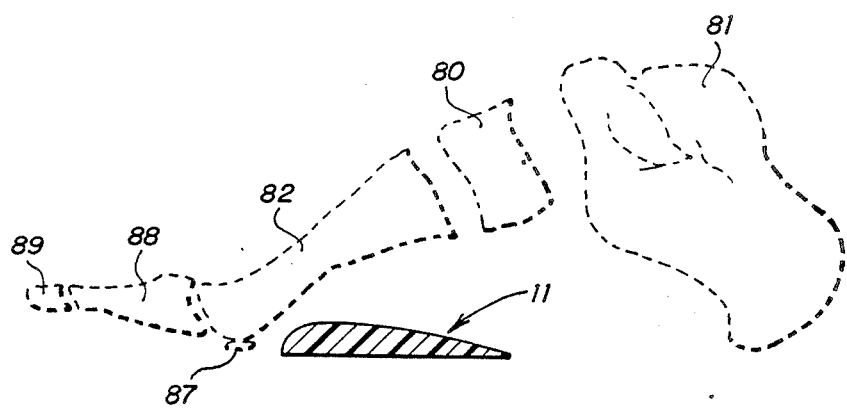
FIG. 6 is a left side sectional view showing the proper relation of the pad to bones of a human foot (shown in phantom lines).

The functional significance of the shape shown in FIGS. 1–4 and detailed in Table I can best be appreciated by reference to FIGS. 5 and 6. A pad 11 according to the invention is shown in proper relationship to the bones of a right human foot, the first through fifth metatarsals of which are shown at 82 through 86. The bones of the tarsus are not shown in detail. One of the sesamoid bones 87 is shown in FIG. 6, and may be considered to be an extension or adjunct of the head of metatarsal 82. Immediately forward of the head of metatarsal 82 is the first phalanx 88 of the big toe, and connected thereto is the second phalanz 89 of the big toe 91. Second through fourth toes 92 through 95 are jointed to heads of metatarsals 82 through 86 respectively.

In FIG. 6 the general relationship of the navicular bone 81 and the cuneiform bones 80 with the metatarsal 82 and other metatarsals is shown. It will be appreciated that stresses on the foot encountered in walking or running on a hard, flat surface will be mainly concentrated at the heel of the foot and the respective heads of the metatarsals 82–86 (including sesamoid bones 87). In many cases the stresses will be particularly concentrated on the heads of the metatarsals.

As seen in FIG. 5 and FIG. 6 the metatarsal pad 11 is supported just posteriorly of the head of the pad 11. In order to give support to all of the metatarsals the front rounded edge 19, 21, and 23 of the pad 11 is shaped in the manner shown and described. The distribution of force and weight provided by a metatarsal pad of the present invention is essentially maximized and far superior to that of prior metatarsal pads which did not accommodate to the shape of the individual heads of the metatarsals, nor to the arcuate orientation of the first through fifth metatarsal heads.

The metatarsal pad of the present invention is firm and relatively incompressible, and thus it is not intended to, and does not function as a cushion in the ordinary sense. Due to the weight distributing shape provided, a cushioning effect is not necessary in conjunction with the metatarsal pad of the present invention. However, soft compressible cushioning of plastic foam, or of latex or rubber, could be employed in conjunction with the pad of the present invention without materially decreasing the advantages of the pad described heretofore.

Any suitable molding technique, such as injection molding or the like, may be employed to manufacture molds according to the invention in mass production. As previously described it is contemplated that the molds would be available in at least five sizes in left and right foot configurations to the orthopedic technician or other person selecting and fitting them. In addition to having adequate ranges of sizes, a certain amount of customizing may be employed by adding a layer of the material for additional lift, varying orientation, or trimming of the pad. Such refinements would not materially change the overall function of the pad in supporting the metatarsals for optimum weight distribution.

In addition to the variations and modifications of the invention which have been described or suggested above, other variations and modifications will be apparent to those skilled in the art, and accordingly the scope of the invention is not to be considered limited to the particular embodiments shown, described, or suggested, but is rather to be determined by reference to the appended claims.

TABLE I x, y, z Surface Coordinates

| | | |
|---|---|---|
| (1) = 0.60, 0.00, 0.00 | (2) = 0.80, 0.00, 0.00 | (3) = 1.00, 0.00, 0.00 |
| (4) = 1.20, 0.00, 0.00 | (5) = 1.40, 0.00, 0.00 | (6) = 1.60, 0.00, 0.00 |
| (7) = 1.80, 0.00, 0.00 | (8) = 2.00, 0.00, 0.00 | (9) = 2.20, 0.00, 0.00 |
| (10) = 2.40, 0.00, 0.00 | (11) = 2.60, 0.00, 0.00 | (12) = 2.80, 0.00, 0.00 |
| (13) = 3.00, 0.00, 0.00 | (14) = 3.20, 0.00, 0.00 | (15) = 3.26, 0.10, 0.00 |
| (16) = 3.28, 0.20, 0.00 | (17) = 3.31, 0.40, 0.00 | (18) = 3.33, 0.60, 0.00 |
| (19) = 3.36, 0.80, 0.00 | (20) = 3.41, 1.00, 0.00 | (21) = 3.45, 1.20, 0.00 |
| (22) = 3.51, 1.40, 0.00 | (23) = 3.58, 1.60, 0.00 | (24) = 3.60, 1.71, 0.00 |
| (25) = 3.40, 1.78, 0.00 | (26) = 3.20, 1.80, 0.00 | (27) = 3.00, 1.90, 0.00 |
| (28) = 2.80, 2.00, 0.00 | (29) = 2.72, 2.00, 0.00 | (30) = 2.60, 2.10, 0.00 |
| (31) = 2.40, 2.15, 0.00 | (32) = 2.27, 2.20, 0.00 | (33) = 2.20, 2.22, 0.00 |
| (34) = 2.00, 2.24, 0.00 | (35) = 1.80, 2.20, 0.00 | (36) = 1.60, 2.12, 0.00 |
| (37) = 1.40, 2.00, 0.00 | (38) = 1.20, 1.84, 0.00 | (39) = 1.15, 1.80, 0.00 |
| (40) = 1.00, 1.72, 0.00 | (41) = 0.80, 1.64, 0.00 | (42) = 0.72, 1.60, 0.00 |
| (43) = 0.60, 1.57, 0.00 | (44) = 0.40, 1.54, 0.00 | (45) = 0.22, 1.48, 0.00 |
| (46) = 0.20, 1.40, 0.00 | (47) = 0.25, 1.20, 0.00 | (48) = 0.31, 1.00, 0.00 |
| (49) = 0.35, 0.80, 0.00 | (50) = 0.40, 0.60, 0.00 | (51) = 0.44, 0.40, 0.00 |
| (52) = 0.49, 0.20, 0.00 | (53) = 0.52, 0.10, 0.00 | (54) = 0.60, 0.20, 0.11 |
| (55) = 0.80, 0.20, 0.10 | (56) = 1.00, 0.20, 0.11 | (57) = 1.20, 0.20, 0.11 |
| (58) = 1.40, 0.20, 0.11 | (59) = 1.60, 0.20, 0.10 | (60) = 1.80, 0.20, 0.10 |
| (61) = 2.00, 0.20, 0.10 | (62) = 2.20, 0.20, 0.10 | (63) = 2.40, 0.20, 0.08 |
| (64) = 2.60, 0.20, 0.08 | (65) = 2.80, 0.20, 0.08 | (66) = 3.00, 0.20, 0.07 |
| (67) = 3.20, 0.20, 0.07 | (68) = 0.60, 0.40, 0.16 | (69) = 0.80, 0.40, 0.16 |
| (70) = 1.00, 0.40, 0.16 | (71) = 1.20, 0.40, 0.16 | (72) = 1.40, 0.40, 0.16 |
| (73) = 1.60, 0.40, 0.16 | (74) = 1.80, 0.40, 0.16 | (75) = 2.00, 0.40, 0.15 |
| (76) = 2.20, 0.40, 0.15 | (77) = 2.40, 0.40, 0.14 | (78) = 2.60, 0.40, 0.13 |
| (79) = 2.80, 0.40, 0.13 | (80) = 3.00, 0.40, 0.12 | (81) = 3.20, 0.40, 0.12 |
| (82) = 0.60, 0.60, 0.20 | (83) = 0.80, 0.60, 0.20 | (84) = 1.00, 0.60, 0.20 |
| (85) = 1.20, 0.60, 0.20 | (86) = 1.40, 0.60, 0.21 | (87) = 1.60, 0.60, 0.21 |
| (88) = 1.80, 0.60, 0.21 | (89) = 2.00, 0.60, 0.20 | (90) = 2.20, 0.60, 0.20 |
| (91) = 2.40, 0.60, 0.18 | (92) = 2.60, 0.60, 0.17 | (93) = 2.80, 0.60, 0.16 |
| (94) = 3.00, 0.60, 0.16 | (95) = 3.20, 0.60, 0.16 | (96) = 0.40, 0.80, 0.15 |
| (97) = 0.60, 0.80, 0.23 | (98) = 0.80, 0.80, 0.22 | (99) = 1.00, 0.80, 0.22 |
| (100) = 1.20, 0.80, 0.23 | (101) = 1.40, 0.80, 0.24 | (102) = 1.60, 0.80, 0.24 |
| (103) = 1.80, 0.80, 0.25 | (104) = 2.00, 0.80, 0.25 | (105) = 2.20, 0.80, 0.24 |
| (106) = 2.40, 0.80, 0.22 | (107) = 2.60, 0.80, 0.21 | (108) = 2.80, 0.80, 0.20 |
| (109) = 3.00, 0.80, 0.19 | (110) = 3.20, 0.80, 0.19 | (111) = 0.40, 1.00, 0.24 |
| (112) = 0.60, 1.00, 0.25 | (113) = 0.80, 1.00, 0.24 | (114) = 1.00, 1.00, 0.25 |
| (115) = 1.20, 1.00, 0.26 | (116) = 1.40, 1.00, 0.27 | (117) = 1.60, 1.00, 0.28 |
| (118) = 1.80, 1.00, 0.28 | (119) = 2.00, 1.00, 0.28 | (120) = 2.20, 1.00, 0.27 |
| (121) = 2.40, 1.00, 0.26 | (122) = 2.60, 1.00, 0.24 | (123) = 2.80, 1.00, 0.22 |
| (124) = 3.00, 1.00, 0.21 | (125) = 3.20, 1.00, 0.21 | (126) = 0.40, 1.20, 0.25 |
| (127) = 0.60, 1.20, 0.25 | (128) = 0.80, 1.20, 0.25 | (129) = 1.00, 1.20, 0.26 |
| (130) = 1.20, 1.20, 0.28 | (131) = 1.40, 1.20, 0.30 | (132) = 1.60, 1.20, 0.31 |
| (133) = 1.80, 1.20, 0.31 | (134) = 2.00, 1.20, 0.31 | (135) = 2.20, 1.20, 0.30 |
| (136) = 2.40, 1.20, 0.29 | (137) = 2.60, 1.20, 0.27 | (138) = 2.80, 1.20, 0.25 |
| (139) = 3.00, 1.20, 0.23 | (140) = 3.20, 1.20, 0.23 | (141) = 3.40, 1.20, 0.15 |
| (142) = 0.40, 1.40, 0.22 | (143) = 0.60, 1.40, 0.23 | (144) = 0.80, 1.40, 0.24 |
| (145) = 1.00, 1.40, 0.26 | (146) = 1.20, 1.40, 0.29 | (147) = 1.40, 1.40, 0.31 |
| (148) = 1.60, 1.40, 0.33 | (149) = 1.80, 1.40, 0.33 | (150) = 2.00, 1.40, 0.33 |
| (151) = 2.20, 1.40, 0.32 | (152) = 2.40, 1.40, 0.31 | (153) = 2.60, 1.40, 0.29 |
| (154) = 2.80, 1.40, 0.26 | (155) = 3.00, 1.40, 0.24 | (156) = 3.20, 1.40, 0.24 |
| (157) = 3.40, 1.40, 0.23 | (158) = 0.80, 1.60, 0.14 | (159) = 1.00, 1.60, 0.22 |
| (160) = 1.20, 1.60, 0.27 | (161) = 1.40, 1.60, 0.31 | (162) = 1.60, 1.60, 0.34 |
| (163) = 1.80, 1.60, 0.34 | (164) = 2.00, 1.60, 0.34 | (165) = 2.20, 1.60, 0.33 |
| (166) = 2.40, 1.60, 0.32 | (167) = 2.60, 1.60, 0.30 | (168) = 2.80, 1.60, 0.27 |
| (169) = 3.00, 1.60, 0.24 | (170) = 3.20, 1.60, 0.22 | (171) = 3.40, 1.60, 0.21 |
| (172) = 1.20, 1.80, 0.17 | (173) = 1.40, 1.80, 0.28 | (174) = 1.60, 1.80, 0.32 |
| (175) = 1.80, 1.80, 0.34 | (176) = 2.00, 1.80, 0.35 | (177) = 2.20, 1.80, 0.34 |
| (178) = 2.40, 1.80, 0.31 | (179) = 2.60, 1.80, 0.28 | (180) = 2.80, 1.80, 0.23 |

TABLE I-continued

| x, y, z Surface Coordinates | | |
|---|---|---|
| (181) = 3.00, 1.80, 0.18 | (182) = 1.60, 2.00, 0.26 | (183) = 1.80, 2.00, 0.30 |
| (184) = 2.00, 2.00, 0.31 | (185) = 2.20, 2.00, 0.30 | (186) = 2.40, 2.00, 0.27 |
| (187) = 2.60, 2.00, 0.20 | (188) = 2.00, 2.20, 0.19 | |

What is claimed is:

1. A metatarsal pad for a human foot and with a y axis extending in a heel to toe direction, an x axis extending in an outside to inside direction and a z axis extending in a down to up direction, comprising:
   a body of resilient substantially incompressible material adapted to be placed in a shoe just posteriorly of the position of the heads of the metatarsal bones of said foot,
   said body having a maximum z axis dimension substantially less than one-third of the x axis of y axis maximum dimension,
   the maximum x axis dimension being more than sufficient to bridge across all five metatarsal bones of the foot, the maximum z dimension at the outside and inside edges being at least one-third of the maximum z dimension,
   the frontal edge being convexly curved in the mid-portion thereof and concavely curved in at least one lateral portion thereof,
   the constant-x cross sections of said body generally having an airfoil-like shape,
   for any x coordinate the maximum z dimension being located at no less than two-thirds of the distance heel to toe of the y axis dimension, and
   the outline of said body viewed in the y direction from the heel having a convex upper middle segment and at least one concave segment adjacent thereto.

2. Apparatus as recited in claim 1 wherein the rear edge of said body extends parallel to the x axis and the upper surface has a z/y slope just forward of said rear edge of 0.25 to 0.5.

3. Apparatus as recited in claim 2 wherein the radius of curvature at the front edge of said body in the y-z plane is from 3/32 to ¼ inch.

4. Apparatus as recited in claim 1 wherein the radius of curvature at the front edge of said body in the y-z plane is from 3/32 to ¼ inch.

5. Apparatus as recited in claim 4 wherein said body width is correlated to adult foot shoe size approximately by $W = 2\frac{1}{8} + S/8$ where W is width in inches and S is American shoe size.

6. Apparatus as recited in claim 1 wherein said body width is correlated to adult foot shoe size approximately by $W = 2\frac{1}{8} + S/8$ where W is width in inches and S is American shoe size.

7. Apparatus as recited in claim 1 wherein the z/x slope of the body upper surface at the inside and outside edges is greater than two.

8. A metatarsal pad for a human foot and with a y axis extending in a heel to toe direction, an x axis extending in an outside to inside direction and a z axis extending in a down to up direction, comprising:
   a body of resilient substantially imcompressible material adapted to be placed in a shoe just posteriorly of the position of the heads of the metatarsal bones of said foot,
   said body having a maximum z axis dimension substantially less than either the x axis or y axis maximum dimension,
   the maximum x axis dimension being sufficient to bridge across all five metatarsal bones of the foot,
   the frontal edge viewed downwardly in the z direction being convexly curved in the mid-portion thereof and concavely curved in at least one lateral portion thereof,
   the front edge of said body viewed in the x direction rising almost vertically and then curving rearward with a radius of curvature from 0.1 to 0.3 inches,
   for any x coordinate the maximum z dimension being located at no less than two-thirds of the distance heel to toe of the y axis dimension, and
   the outline of said body viewed in the y direction from the heel having a convex upper middle segment and at least one concave segment adjacent thereto.

9. Apparatus as recited in claim 8 wherein the maximum z dimension at the outside and inside edges is at least one-third of the overall maximum z dimension.

10. Apparatus as recited in claim 9 wherein the radius of curvature at the front edge of said body in the y-z plane is from 3/32 to 174 inch.

11. Apparatus as recited in claim 8 wherein the radius of curvature at the front edge of said body in the y-z plane is from 3/32 to ¼ inch.

12. Apparatus as recited in claim 8 wherein said body width is correlated to adult foot shoe size approximately by $W = 2\frac{1}{8} + S/8$ where W is width in inches and S is American shoe size.

13. Apparatus as recited in claim 8 wherein the z/x slope of the body upper surface at the inside and outside edges is greater than two.

14. A metatarsal pad for a human foot and with a y axis in a heel to toe direction, an x axis in an outside to inside direction and a z axis in a down to up direction, comprising:
   a body of substantially incompressible material adapted to be placed in a shoe just posteriorly of the position of the heads of the metatarsal bones of said foot,
   said body having a maximum z axis dimension less than the x axis maximum dimension,
   the maximum x axis dimension being more than sufficient to bridge across at least the first three metatarsal bones of the foot,
   the frontal edge being convexly curved in the mid-portion thereof and concavely curved in at least one lateral portion thereof,
   the front edge of said body viewed in the x direction rising almost vertically and then curving rearward with a radius of curvature from 0.1 to 0.3 inches,
   for any x coordinate the maximum z dimension being located at no less than one-half of the distance heel to toe of the y axis dimension, and
   the outline of said body viewed in the y direction from the heel having a convex upper middle segment.

15. Apparatus as recited in claim 14 wherein the outline of said body viewed in the y direction from the heel has a concave segment adjacent said convex upper middle segment.

16. Apparatus as recited in claim 14 wherein the rear edge of said body extends parallel to the x axis and the upper surface has a z/y slope just forward of said rear edge of 0.25 to 0.5.

17. Apparatus as recited in claim 16 wherein the radius of curvature at the front edge of said body in the y-z plane is from 3/32 to ¼ inch.

18. Apparatus as recited in claim 14 wherein the radius of curvature at the front edge of said body in the y-z plane is from 3/32 to ¼ inch.

19. Apparatus as recited in claim 14 wherein said body width is correlated to adult foot shoe size approximately by $W = 2\frac{1}{8} + S/8$ where W is width in inches and S is American shoe size.

20. Apparatus as recited in claim 14 wherein the maximum x axis dimension is sufficient to bridge at least four metatarsal bones of the foot.

* * * * *